US010967379B2

(12) United States Patent
Butler et al.

(10) Patent No.: US 10,967,379 B2
(45) Date of Patent: Apr. 6, 2021

(54) INCUBATOR STAND AND INCUBATOR DOCKING SYSTEM

(71) Applicant: Planer Limited, Sunbury (GB)

(72) Inventors: Stephen James Butler, Wokingham (GB); Stephen Mark Joseph Wilkins, London (GB)

(73) Assignee: Planer Limited, Sanbury (GB)

( * ) Notice: Subject to any disclaimer, the term of this patent is extended or adjusted under 35 U.S.C. 154(b) by 492 days.

(21) Appl. No.: 15/711,677

(22) Filed: Sep. 21, 2017

(65) Prior Publication Data

US 2018/0104697 A1    Apr. 19, 2018

(30) Foreign Application Priority Data

Sep. 27, 2016 (GB) ...................................... 1616403

(51) Int. Cl.
*B01L 9/00* (2006.01)
*C12M 3/00* (2006.01)
(Continued)

(52) U.S. Cl.
CPC ............... *B01L 9/52* (2013.01); *C12M 23/44* (2013.01); *C12M 23/48* (2013.01); *C12M 23/50* (2013.01);
(Continued)

(58) Field of Classification Search
CPC ....... B01L 2200/025; B01L 2300/0809; B01L 9/52; C12M 23/44; C12M 23/48; C12M 23/50
See application file for complete search history.

(56) References Cited

U.S. PATENT DOCUMENTS

| 3,188,157 A | 6/1965 | Rand |
| 2005/0003525 A1 | 1/2005 | Hsu |

(Continued)

FOREIGN PATENT DOCUMENTS

| DE | 202009017633 U1 | 5/2010 |
| EP | 1 364 753 A1 | 11/2003 |

(Continued)

OTHER PUBLICATIONS

Search Report Under Section 17 for Application No. GB1616403.0, dated Jun. 19, 2017, 2 pages, United Kingdom.
(Continued)

*Primary Examiner* — Gautam Prakash
*Assistant Examiner* — Lydia Edwards
(74) *Attorney, Agent, or Firm* — Stinson LLP

(57) ABSTRACT

An incubator stand for holding a plurality of incubators in a stacked arrangement, the incubator stand comprising: a stand base; a shaft element upstanding from the stand base; and a plurality of incubator bases rotatably received on the shaft element, each incubator base forming a support for or forming part of an incubator. A stop element is also provided which prevents or limits angular displacement of each incubator base, so that each incubator base can be pivoted out from a stack of said incubator bases to in use access an incubator associated therewith without causing the stack to topple. An incubator docking system and incubator system for transferring incubators between different environmental conditions are also provided.

12 Claims, 7 Drawing Sheets

(51) Int. Cl.
*C12M 1/00* (2006.01)
*B01L 99/00* (2010.01)

(52) U.S. Cl.
CPC . *B01L 2200/025* (2013.01); *B01L 2300/0809* (2013.01)

(56) References Cited

U.S. PATENT DOCUMENTS

| | | |
|---|---|---|
| 2006/0154232 A1 | 7/2006 | Degel et al. |
| 2009/0037031 A1 | 2/2009 | George et al. |
| 2015/0010996 A1* | 1/2015 | Tsunnura ............... C12M 23/10 435/303.1 |

FOREIGN PATENT DOCUMENTS

| | | |
|---|---|---|
| WO | 2007/050088 A2 | 5/2007 |
| WO | 2013/106751 A1 | 7/2013 |

OTHER PUBLICATIONS

Examination Report Under Section 18(3) for Application No. GB1616403.0, dated Sep. 8, 2017, 1 page, United Kingdom.

\* cited by examiner

INCUBATOR STAND AND INCUBATOR DOCKING SYSTEM

RELATED APPLICATIONS

This application claims the benefit under 35 U.S.C. § 119(a)-(d) of British Patent Application No. 1616403.0 filed on 27 Sep. 2016, the disclosure of which is incorporated by reference.

FIELD OF THE TECHNOLOGY

The present invention relates to an incubator stand for holding a plurality of incubators in a stacked arrangement, particularly but not necessarily exclusively for the use of allowing convenient ease of access to at least one incubator that requires monitoring in a laboratory environment. The invention further relates to an incubator docking system, and to an incubator system for transferring incubators between different environmental conditions.

BACKGROUND OF THE INVENTION

Incubators are widely used in laboratories around the world for applications requiring a carefully controlled environment, controlling for variables such as temperature, gas composition and humidity. Often, laboratories will have a plurality of operational incubators with the aim of creating and monitoring several environments simultaneously.

Typically, incubators are formed as large temperature-controlled units into which a sample to be incubated is directly insertable, in order to maintain environmental conditions therein. Such incubators typically require regular checking and may be provided with an optical inspection portion through which the user can view the sample therein. Not only are these incubators bulky, taking a large amount of physical area on a laboratory bench, but the need to provide optical access of the samples prevents the incubators from being stacked on top of one another, notwithstanding the physical challenge in doing so.

Furthermore, incubators may require a fluid supply and/or electrical wiring in order to maintain a specific gas composition, humidity or similar. If multiple incubators are stacked, each with separate conduits, the conduits may become entangled causing confusion or there may be insufficient space to accommodate all of the conduits. Similarly, the incubators may require an electrical-wiring loom in order to provide an electricity supply for heating, lighting or similar. If multiple incubators are stacked, each with separate electrical wiring looms, the looms may become entangled causing confusion or there may be insufficient space to accommodate all of the looms.

SUMMARY OF THE INVENTION

The present invention seeks to provide an incubator stand and docking system to obviate or substantially limit the above-referenced problems.

According to a first aspect of the invention there is provided an incubator stand for holding a plurality of incubators in a stacked arrangement, the incubator stand comprising: a stand base; a shaft element upstanding from the stand base; a plurality of incubator bases rotatably received on the shaft element, each incubator base forming a support for or forming part of an incubator; and a stop element which prevents or limits angular displacement of each incubator base, so that each incubator base can be pivoted out from a stack of said incubator bases to in use access an incubator associated therewith without causing the stack to topple.

The stand base allows for the incubator stand to be supported, whilst the shaft element gives a point for the incubator bases to rotate around. The incubator bases being rotatably received allow for one incubator to be selected and pivotably moved to a position away from the other incubators in the stack where it can be checked. This allows for a compact stack of incubators to be constructed without compromising the environment around incubated samples, since optical access to the samples can still be readily achieved.

Preferably, each incubator base may have a maximum width which is less than a maximum width of the stand base, the stop element preventing or limiting angular displacement of each incubator base beyond the maximum width of the stand base. The stand base may taper in a converging direction towards the shaft element, in which case, the stand base may be or substantially be triangular-shaped, the shaft element being at or adjacent to an apex of the stand base.

The incubator base having a maximum width less that that maximum width of the stand base allows for the incubator bases to be moved relative to each other around the shaft whilst still remaining within the projected width of the stand base. The stop element ensures that the incubator base is not able to be moved outside of the projected width of the stand base and thus ensures that the system does not have a centre of mass outside of the stand base and so does not cause the stack to topple. Advantageously, the stand base is or is substantially triangular shaped, the shaft element being at or adjacent to an apex of the stand base. Such a configuration would allow for a spatial optimization of the size of the stand base to be achieved whilst still allowing the incubator base a full range of angular displacement about the shaft without being outside of the projected width of the base. This may ensure that the incubators can be checked conveniently without them causing the incubator stand to topple.

The incubator stand may further comprise a fluid-supply conduit which extends from the stand base, and said fluid-supply conduit may be upstanding from the stand base at or adjacent to or substantially in parallel with the shaft element. Secondary conduits may extend from the fluid-supply conduit to fluidly connect each incubator base with the fluid-supply conduit, in which case, each fluid-supply conduit may be received within the stop element.

Optionally, the incubator stand may further comprise an electrical-wiring loom which extends from the stand base. The electrical-wiring loom may preferably extend at or adjacent to the shaft element. Electrical spurs may extend from the electrical-wiring loom to electrically connect each incubator base with the electrical-wiring loom and, furthermore, the electrical-wiring loom may be received within the stop element.

The provision of a fluid or electrical manifold inside the incubator stand which is sufficiently resilient to the pivoting of the incubator bases is beneficial, since it means that an electrical and/or fluid supply can be provided to the incubators in use very easily using the axis of the shaft element.

Optionally, one said stop element may be provided associated with each incubator base.

By providing a stop element with each incubator base, each incubator can be moved independently of the others, allowing selective access to the or each incubator in use.

In a preferred embodiment, each incubator base may be or form part of a caddy for releasably receiving an incubator thereon. Each caddy may include a fluid inlet port and a fluid outlet port in fluid communication with a or the fluid-supply conduit extending from the stand base, and which are fluid-tightly releasably engagable with corresponding incubator ports on a said incubator.

It is beneficial for the fluid-shut-off valve to be at or adjacent to the fluid inlet port and/or fluid outlet port, and to have a closure activation element which operates the fluid-shut-off valve on release of an incubator from the caddy. This advantageous arrangement would allow for an in use incubator, with a supply of fluid, to be removed from the caddy without causing a leak of fluid from the fluid conduit system.

The incubator stand may further comprise a fluid shut-off valve at or adjacent to the fluid inlet port and/or fluid outlet port, and a closure activation element which operates the fluid shut-off valve on release of the said incubator from the caddy. Each caddy may additionally or alternatively include at least one electrical connector in electrical communication with a or the said electrical-wiring loom extending from the stand base, and which is electrically releasably engagable with a corresponding connector of the said incubator from the caddy.

It is beneficial for the fluid-shut-off valve to be at or adjacent to the fluid inlet port and/or fluid outlet port and a closure activation element which operates the fluid-shut-off valve on release of an incubator from the caddy. This advantageous arrangement would allow for an in use incubator, with a supply of fluid and/or electricity, to be removed from the caddy without causing a leak of fluid from the fluid conduit system.

The incubator stand may further comprise a releasable locking element for releasably engaging the caddy and an incubator, the releasable locking element comprising at least one hooked arm which is automatically latchable with a receiver on the said incubator.

This arrangement allows for the incubator to be attached to the caddy and therefore may prevent the incubator from being unintentionally removed from the caddy.

Preferably, the stop element may define a maximum angular displacement of each of the plurality of incubator bases of no more than 90 degrees, which may be of or substantially of 60 degrees.

Such an angular arrangement allows a reasonable range of movement for each incubator base to be provided without significantly increasing the operational volume of the incubator docking system.

According to a second aspect of the invention, there is provided an incubator docking system comprising: an incubator stand having: a stand base; a shaft element upstanding from the stand base; a plurality of incubator bases rotatably received in a spaced relationship on the shaft element, each incubator base being formed as a caddy having a maximum width which is less than a maximum width of the stand base; and a stop element which prevents of limits angular displacement of each caddy beyond the maximum width of the stand base; and at least one incubator which is releasably engagable with a said caddy of the incubator stand; each caddy being pivotable relative to the other caddies to in use access an incubator associated therewith without causing the incubator stand to topple.

The incubator docking system may further comprise a fluid-supply conduit which extends from the stand base and is fluidly engagable with each caddy to provide a fluid supply to an incubator engaged therewith, and/or the incubator docking system may further comprise an electrical-wiring loom which extends from the stand base and is electrically engagable with each caddy to provide power to an incubator engaged therewith.

According to a third aspect of the invention, there is provided an incubator system comprising a first incubator docking system, preferably in accordance with the second aspect of the invention, and a second incubator docking system, preferably in accordance with the second aspect of the invention, the second incubator docking system being located in a fume hood environment; wherein the at least one incubator is releasably transferable between the first and second incubator docking systems without opening the at least one incubator to expose an incubated sample therein.

By providing a means by which an incubator can be transferred between different working environments, it becomes feasible to transfer samples without compromising the carefully engineering working conditions inside the incubator; in current systems, the incubator is either too bulky to move, or would require opening of the incubator to access the samples therein.

BRIEF DESCRIPTION OF FIGURES

The invention will now be more particularly described, with reference to the accompanying drawings, in which.

DETAILED DESCRIPTION

Figure 1:
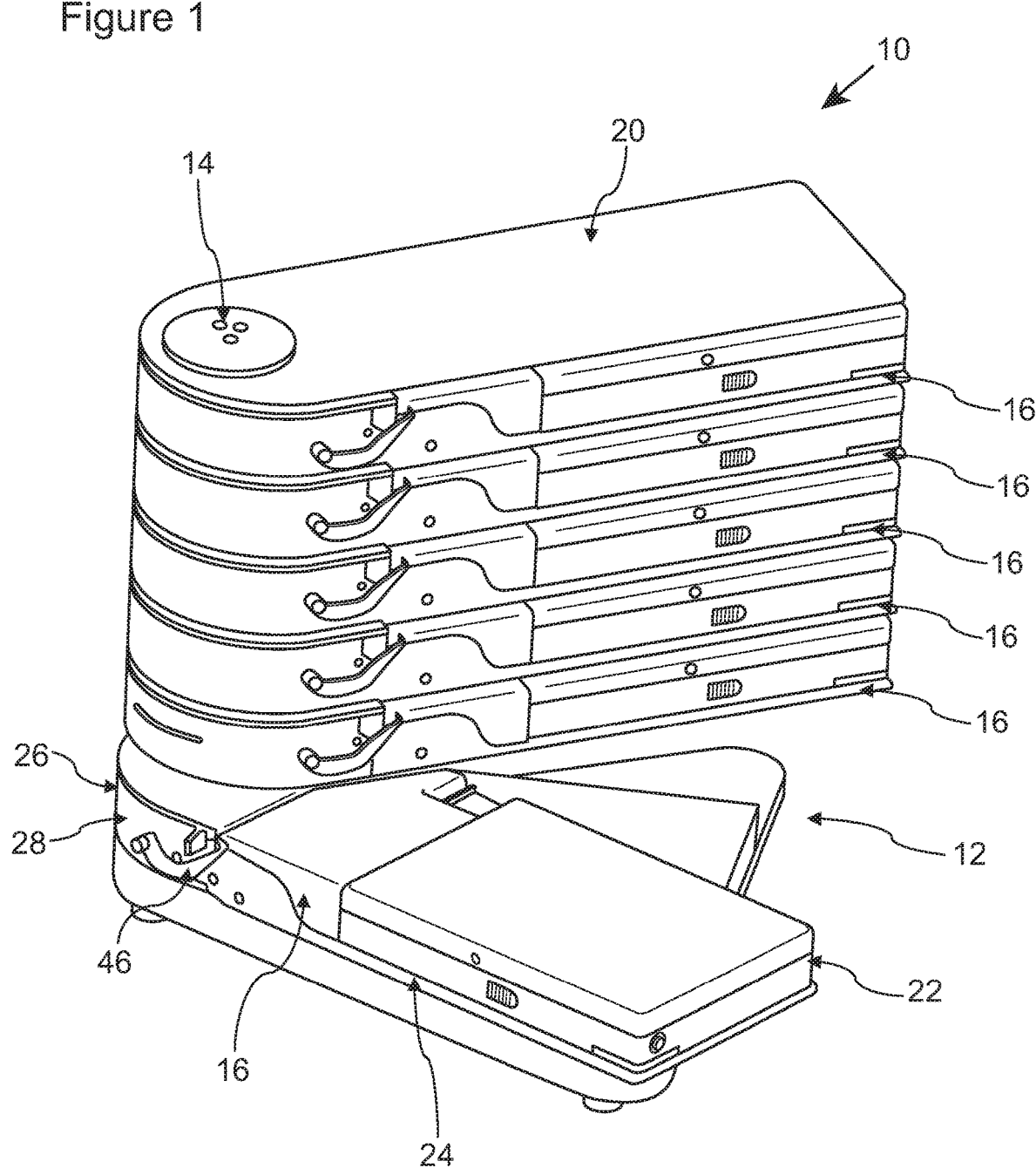
FIG. 1 shows a perspective view of a first embodiment of an incubator stand in accordance with the first aspect of the invention, with one incubator base pivoted out relative to the other incubator bases.
Figure 2:
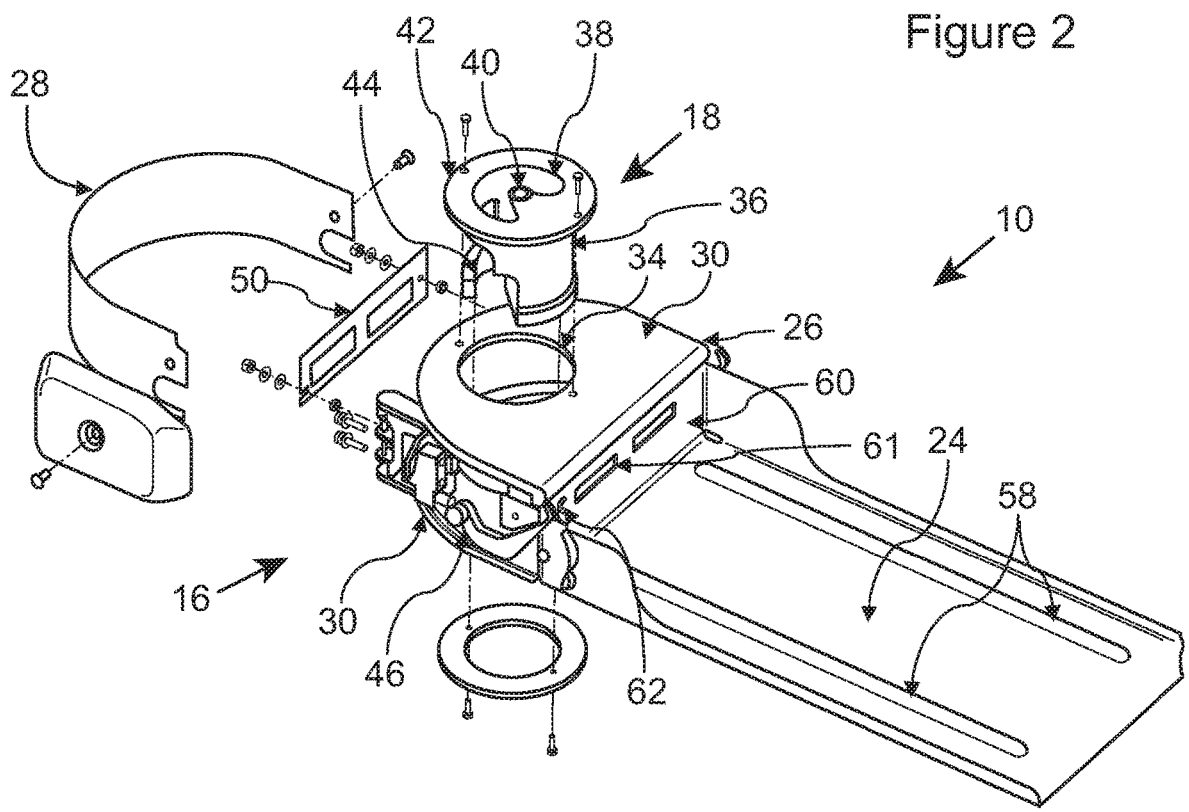
FIG. 2 shows an exploded perspective view of the incubator base of FIG. 1.

Referring firstly to FIGS. 1 and 2 of the drawings, there is shown an incubator stand, indicated globally at 10. The incubator stand 10 comprises a stand base 12, a shaft element 14 upstanding from the stand base 12, at least one, and preferably a plurality of incubator bases 16 which are rotatably received on the shaft element 14, and a stop element 18 which prevents or limits the angular displacement of each incubator base 16. There is a cap or cover element 20 which is positioned preferably at the top of the shaft element 14. A plurality of incubators 22 are also illustrated, which are here releasably engagable with corresponding incubator bases 16. The incubator bases 16 may themselves be releasably engagable with the shaft element 14, or may alternatively be fixed in position on the shaft element 14. An incubator base 16 is shown in detail in FIG. 2. The incubator base 16 comprises, at one end, a platform element 24 for supporting and/or holding an incubator 22 in position relative to the stand base 12. The platform element 24 extends from a hub or head portion 26 within which may be housed operational components of the incubator base 16, in particular those which are arranged to couple with an in use incubator 22. Preferably, each incubator 22 is a self-contained incubator unit.

This head portion 26 is substantially D-shaped, here having an arcuate rear cover 28 which is positionable between two parallel or substantially parallel hub walls 30 to define a cavity 32 therebetween. In each of the hub walls 30, there is provided an aperture 34 within which the stop element 18 is receivable, which is here formed as a collar 36 which bridges the cavity. The collar 36 is substantially cylindrical in shape with an arcuate longitudinal, preferably C-shaped, channel 38 extending or substantially extending therethrough. A further shaft bore 40 is also provided through the collar 36 which is receivably engagable about the shaft element 14 of the stand base 12.

The collar 36 is preferably formed from a plastics material and has a lip or rim 42 at one end thereof which is complementarily seatable onto one or other hub wall 30. The collar 36 may further have an opening 44 on at least part of a circumferential surface which is in communication with the channel 38 and from which elements within the channel 38 may protrude or extend into the cavity 32. The collar 36 may therefore define a stop of the stop element 18 as being the angular extent of the channel 38 relative to the shaft bore 40.

At either end of the rear cover 28 of the head portion 26 may preferably be provided at least one, and preferably two, fixed releasable locking elements 46. Each locking element 46 may be interengagable with an incubator 22 which has been connected to the respective incubator base 16. Preferably, the locking element 46 may be formed as a sprung latch, here having a dog-legged shape or being cranked so as to form a return 48 which can engage with a complementary engagement portion on the incubator 22.

Between the collar 36 and the platform element 24 there may be provided one or more electrical spurs and at least one fluid supply conduit; these items are not illustrated for ease, but will be engagable with the respective electrical connection interface 50 and fluid inlet and outlet ports 52, 54 for engagement with the incubator 22. The fluid inlet and/or outlet ports 52, 54 form part of a fluid shut-off valve 56 of the incubator base 16 to selectively control fluid transit from the incubator base 16 an associated incubator 22. This will be discussed in more detail below.

The platform element 24 is preferably formed as a rectangular or substantially rectangularly-shaped base which extends longitudinally from the head portion 26 and is shaped so as to match or substantially match a base area of an associated incubator 22, and the incubator base 16 may therefore be beneficially formed as a caddy within which a corresponding incubator 22 is receivable.

There may be provided one or more ridges 58 that run along the length of the platform element 24 and are spaced close to either side of the longitudinal direction of the platform element 24; two such ridges 58 can be seen in FIG. 2. These ridges 58 may assist with the fitting of the incubator 22 into the incubator base 16. A panel wall 60 that joins the head portion 26 and the platform element 24 here has first and second apertures 61 which are co-operable with the electrical connection interface 50 and first and second circular apertures 62 to accommodate engagement with the fluid shut-off valve 56. It will be clear, however, that the precise form of the panel wall 60 will be determined by the electrical and fluid interfaces of the incubator 22 used with the incubator stand 10.

Figure 3:
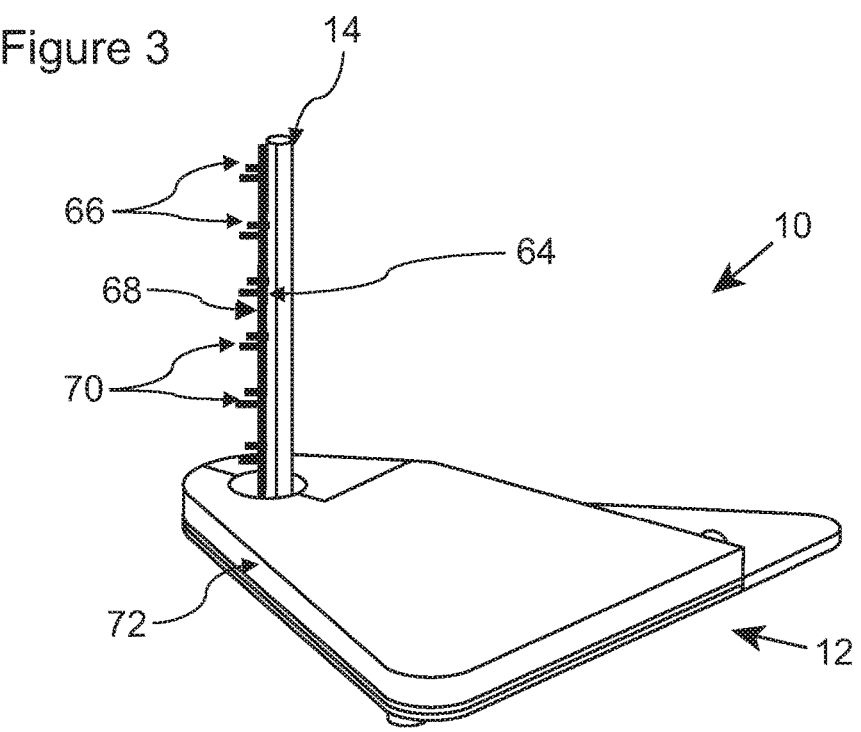
FIG. 3 shows a perspective view of the incubator stand of FIG. 1.

Referring to FIG. 3 there is shown the stand base 12, the shaft element 14, a fluid supply conduit 64 having a plurality of secondary conduits 66 extending therefrom, and an electrical wiring loom 68 having a plurality of electrical spurs 70 extending therefrom. Each of the secondary conduits 66 and electrical spurs 70 may be formed so as be positionable at or adjacent to a level of an incubator base 16 when engaged with the shaft element 14.

The shaft element 14 is upstanding from the stand base 12 and the shape of the stand base 12 may preferably taper in a converging direction towards the shaft element 14, thereby forming a triangular or substantially triangular base area. As such, the shaft element 14 may be upstanding from an apex of the triangle. The fluid supply conduit 64 and the electrical wiring loom 68 both run adjacent to and in parallel with the shaft element 14. The stand base 12 may have a raised section 72 that may contain control circuitry, a further fluid conduit or conduits for the introduction of the fluid into the system and a further electrical loom or looms for introduction of electricity into the system. The stand base 12 may be weighted to aid stability.

It will be appreciated that, for stability purposes, each incubator base 16 may have a maximum width which is less than a maximum width of the stand base 12, the stop element 18 preventing or limiting angular displacement of each incubator base 16 beyond the maximum width of the stand base 12. The stop element 18 may define a maximum angular displacement of each of the plurality of incubator bases 16 of no more than 90 degrees, and may preferably define a maximum angular displacement of each of the plurality of incubator bases 16 of or substantially of 60 degrees, which matches or substantially matches an angular range of the triangular shape of the stand base 12.

Figure 4:
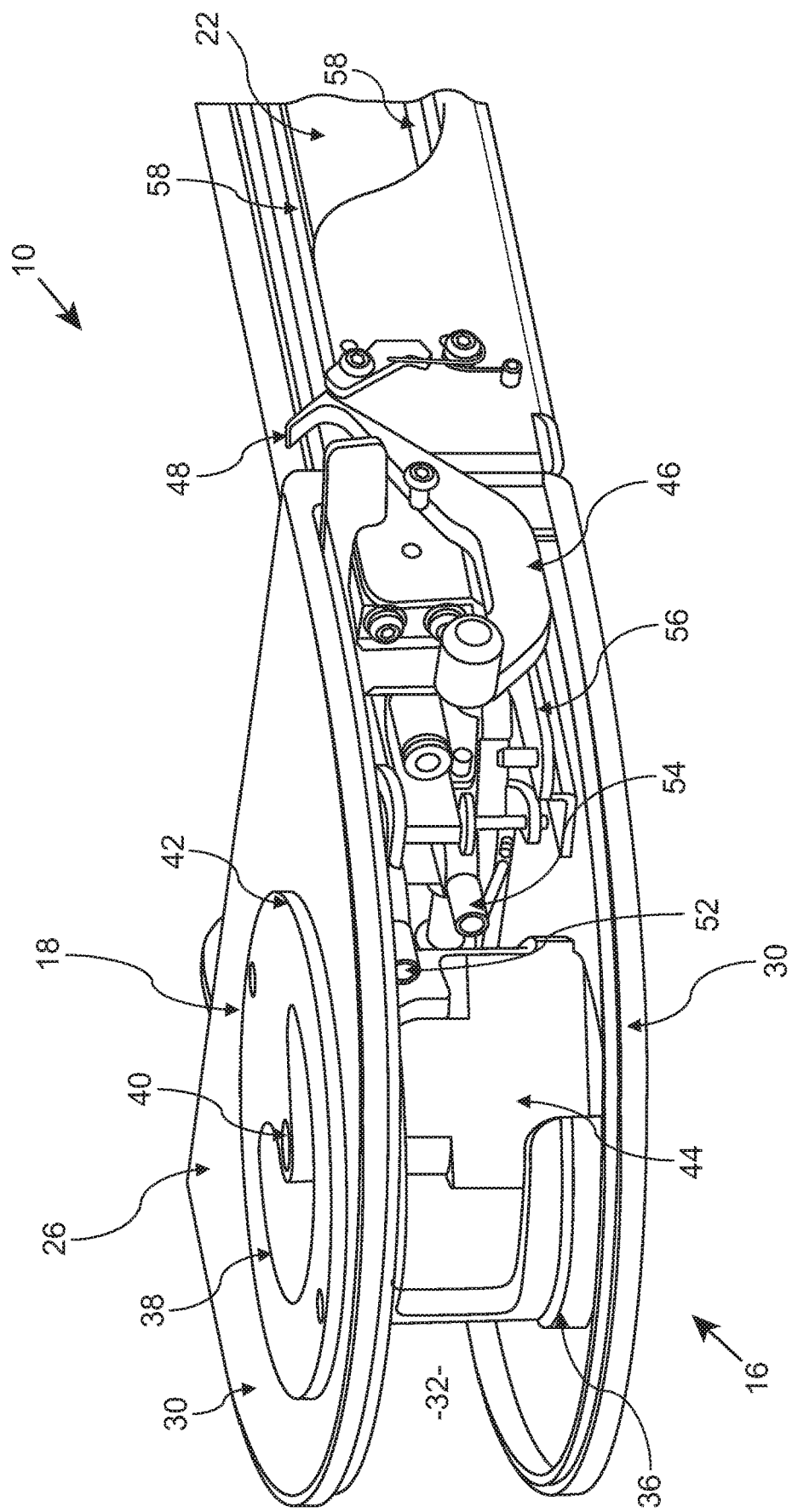
FIG. 4 shows a rear perspective view of the incubator base of FIG. 2 with the releasable locking element and fluid shut off valve shown.
Figure 5:
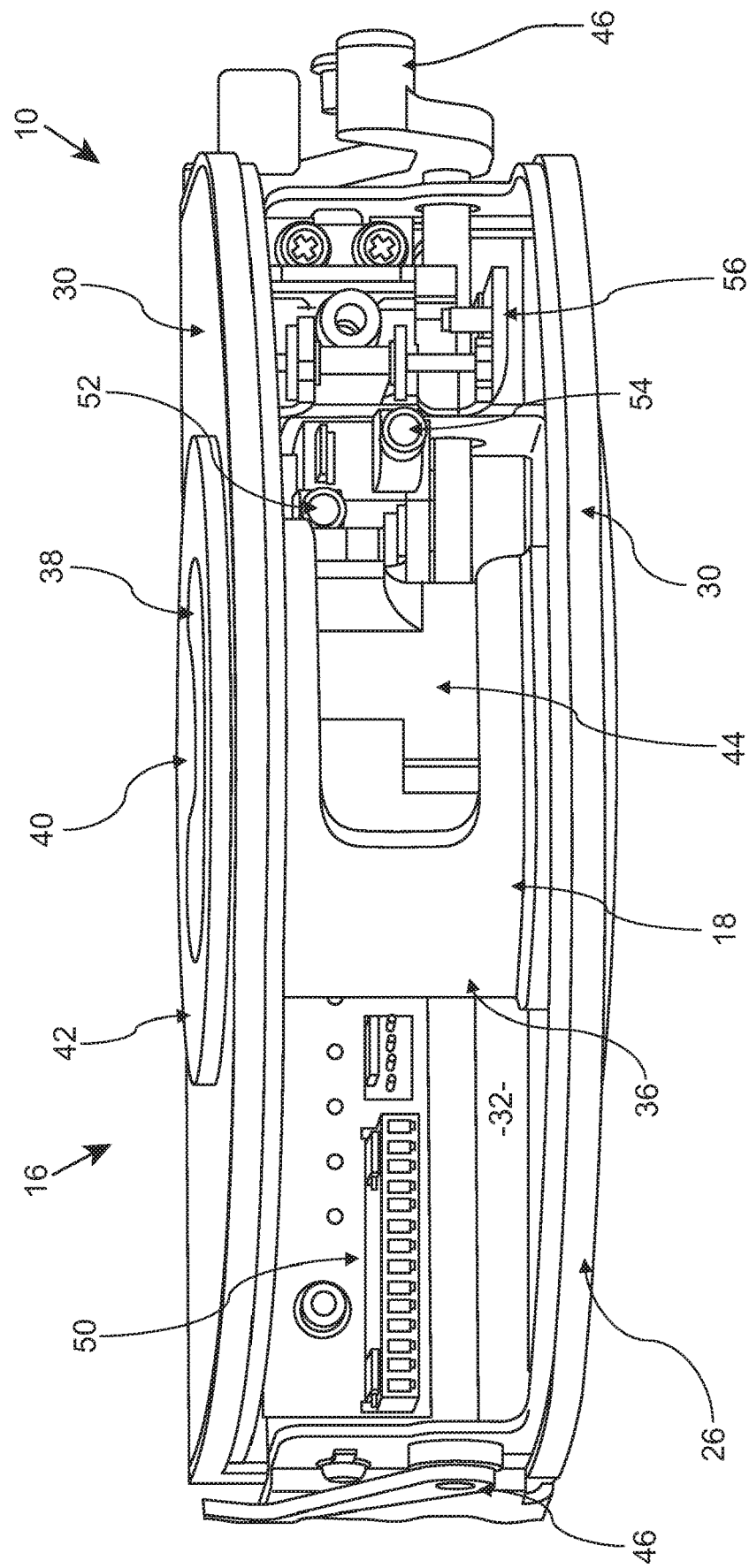
FIG. 5 shows a further rear perspective view of the incubator base of FIG. 2 with the fluid inlet and outlet ports shown along with the electrical connector thereof.

FIGS. 4 and 5 show the assembled incubator base 16 in more detail with the rear cover 28 removed. In particular, the in situ positions of the fluid shut-off valve 56, collar 36 and electrical connector interface 50 within the cavity 32 can be seen in more detail. In particular, more detail of the circumferential opening 44 of the collar 36 can be seen; the secondary conduit 66 and electrical spur 70 associated with the incubator base 16 can extend through the circumferential opening 44 without being disturbed or significantly affected even whilst the incubator base 16 is pivoted about the shaft element 14.

Figure 6:
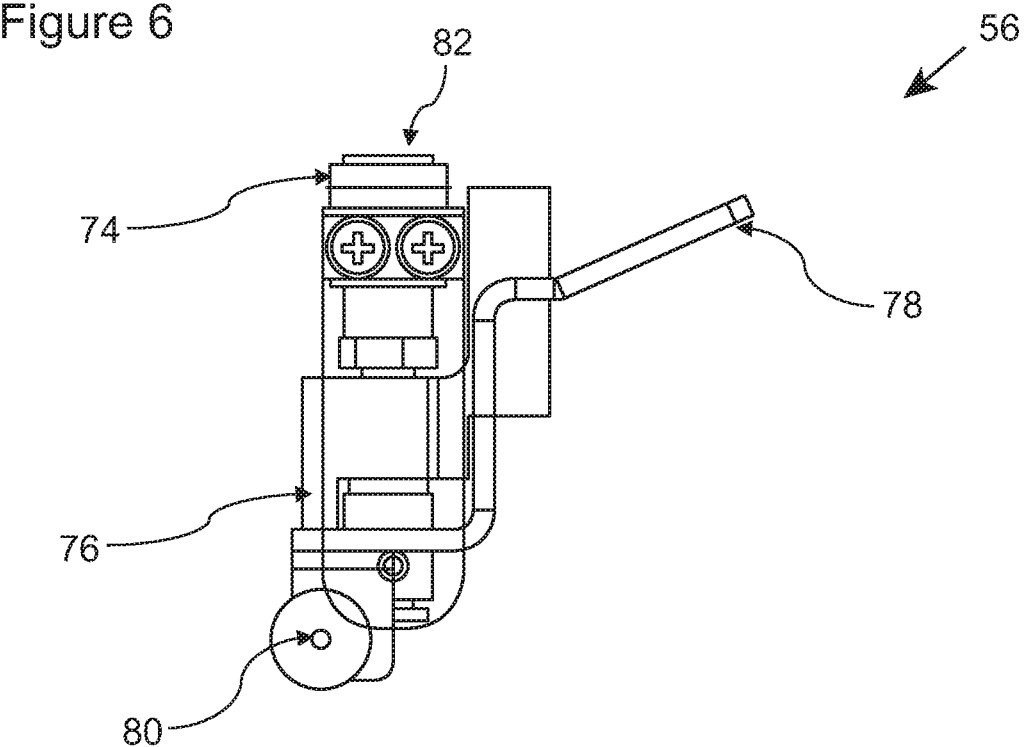
FIG. 6 shows a plan view of the fluid shut-off valve of the incubator base of FIG. 2 in a "closed" position.

Referring to FIG. 6 there is shown the fluid shut off valve 56 in a closed position. The fluid shut off valve 56 comprises a piston 74 or similar actuator which is fixedly engaged with a valve frame 76, for the opening and closing of the fluid shut-off valve 56 to an engaged incubator 22. A lever element 78 is also provided, which is engaged with the piston 74 and is able to change its position. A pivot 80 is provided at the opposite end from the piston 74 of the fluid shut-off valve 56, around which the lever element 78 moves, the pivot 80 here including a roller to ease the movement of the lever element 78. In the condition shown in FIG. 6, no incubator 22 is engaged with the incubator base 16, and therefore there is no force applied to the lever element 78. As such the piston 74 is fully extended, which seals a passage of fluid across the end 82 of the fluid shut-off valve 56, which in turn prevents fluid passing out of the incubator base 16.

Figure 7:
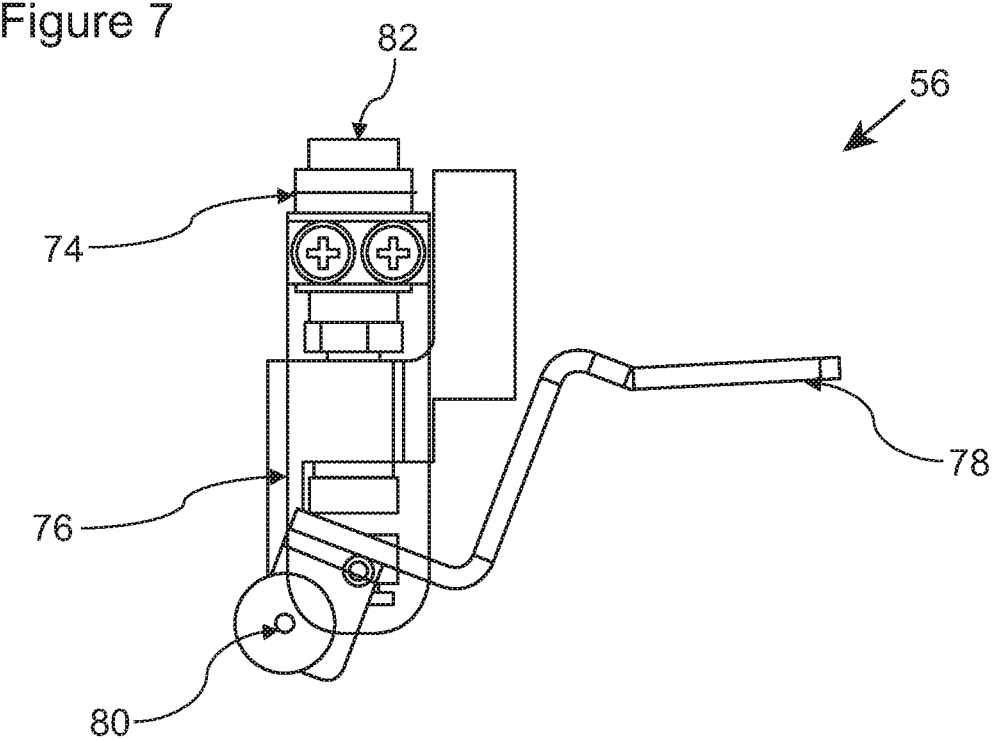
FIG. 7 shows a plan view of the fluid shut off valve of the incubator base of FIG. 2 in an "open" position.

FIG. 7 shows the fluid shut-off valve 56 in an open position. In this condition, an incubator 22 has been engaged with the incubator base 16 which has contacted with and urged the lever element 78 out of its default position. In doing so, the piston 74 has been retracted, creating an opening at the end 82 of the fluid shut-off valve 56 through which fluid may pass into the incubator 22. This arrangement advantageously means that fluid flow can only be activated into the incubator 22 once it has been correctly engaged with the incubator base 16.

To use the incubator stand 10, an incubator base 16 can be pivoted about the shaft element 14 until the platform element 24 is fully accessible. An incubator 22 may then be inserted or removed from the incubator base 16 by decoupling therefrom, usually by disengagement of the locking element 46. This means that a plurality of incubators 22 can be readily stacked and stored, all whilst providing adequate electrical and fluid supplies, whilst still allowing access to a single incubator 22 in the stack when interrogation of the samples is required. The arrangement of the incubator stand 10 is such that, regardless of the angular position of any of the incubator bases 16 in the stack, the incubator stand 10 will not topple. Such an incubator stand 10 can therefore be safely used on a laboratory benchtop.

The in use incubators 22 are coupled with incubator bases 16 in a stack in the incubator stand 10. This is achieved by placing an incubator 22 in front of the platform element 24 of the incubator base 16, which may be simplified by lining up the ridges 58 on the platform element 24 with corresponding grooves on the incubator 22, and pushing the incubator 22 along the platform element 24 until full engagement is achieved. The locking elements 46 can then lock the incubator 22 into place onto the incubator base 16.

The electrical connectors on the incubator base 16 are allowed access, through the electrical connector interface 50, to contact electrical contacts on the incubator 22 itself. The fluid inlet and/or outlet ports 52, 54 are allowed access through the circular apertures 62 to connect with corresponding fluid inlet and outlet ports on the incubator 22 itself. In this way the incubator 22 is connectable to the electricity and fluid supply of the incubator stand 10.

The fluid conduit and the electrical looms with the raised section of the stand base 12 may be attached to an external fluid and electricity supply, respectively. This allows the system to be supplied with electricity and fluid.

Each incubator base 16, when the incubator 22 is fitted to said incubator base 16, is able to rotate around the shaft element 14. Attached incubator bases 16 are able to rotate around the shaft element 14 relative to each other and once an incubator base 16 is rotated to a position around the shaft element 14 whereby the top of the attached incubator 22 is not blocked by incubator bases 16 above it, the incubator 22 is able to be opened and checked.

The incubator bases 16 are not able, in this instance, to be rotated around the shaft element 14 beyond the maximum projected width of the stand base 12. This ensures that the centre of mass of the incubator docking system formed by the incubator stand 10 and at least one incubator 22 does not fall outside of the width of the stand base 12 so that the incubator stand 10 does not topple. This limit of angular displacement is caused by the stop element 18.

The incubators 22 are able to be removed from their respective incubator bases 16 for cleaning. This is done by releasing the releasable locking elements 46 and then sliding the incubator 22 from the platform element 24 of the incubator base 16. On releasing the releasable locking elements 46 the fluid shut-off valve 56 also closes which stops fluid from flowing out through the incubator base 16, meaning that fluid does not spill out of the system once the incubator 22 is decoupled.

Figure 8:
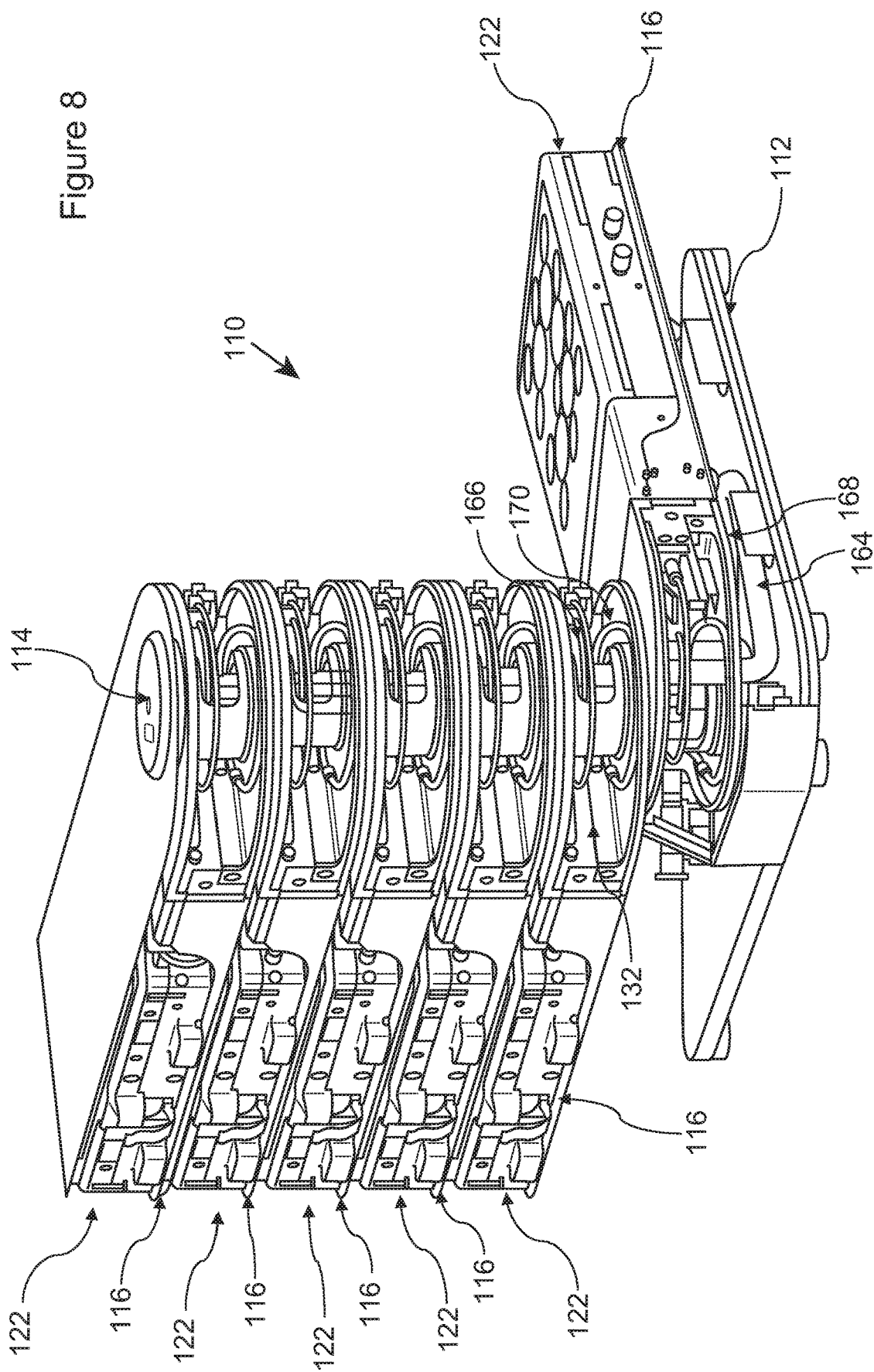
FIG. 8 shows a perspective representation of a second embodiment of an incubator stand in accordance with the first aspect of the invention whereby the in use incubators are not removable.

FIG. 8 shows a second embodiment of the incubator stand, indicated globally at 110 wherein the incubators 122 are not removable from their respective incubator bases 122. In other respects, the incubator stand 110 is similar to that described above, and identical and/or similar components will be referred to using identical and/or similar reference numerals, and further detailed description will be omitted for brevity.

The incubator stand comprises a stand base 112, a shaft element 114 and a plurality of incubator bases 116. Within the cavity 132 of each incubator base 116 is provided two arcuate secondary conduits 166 extending from the fluid supply conduit 164, and at least one electrical spur 170 extending from the electrical connector 168.

Given that the incubators 122 cannot be removed from the incubator bases 116, it is not possible to extract each incubator 122 for separate interrogation; however, in the pivoted position, as indicated by the lowermost incubator 122 in FIG. 8, optical access to each sample is attainable, and microscopy may therefore be possible.

Figure 9:
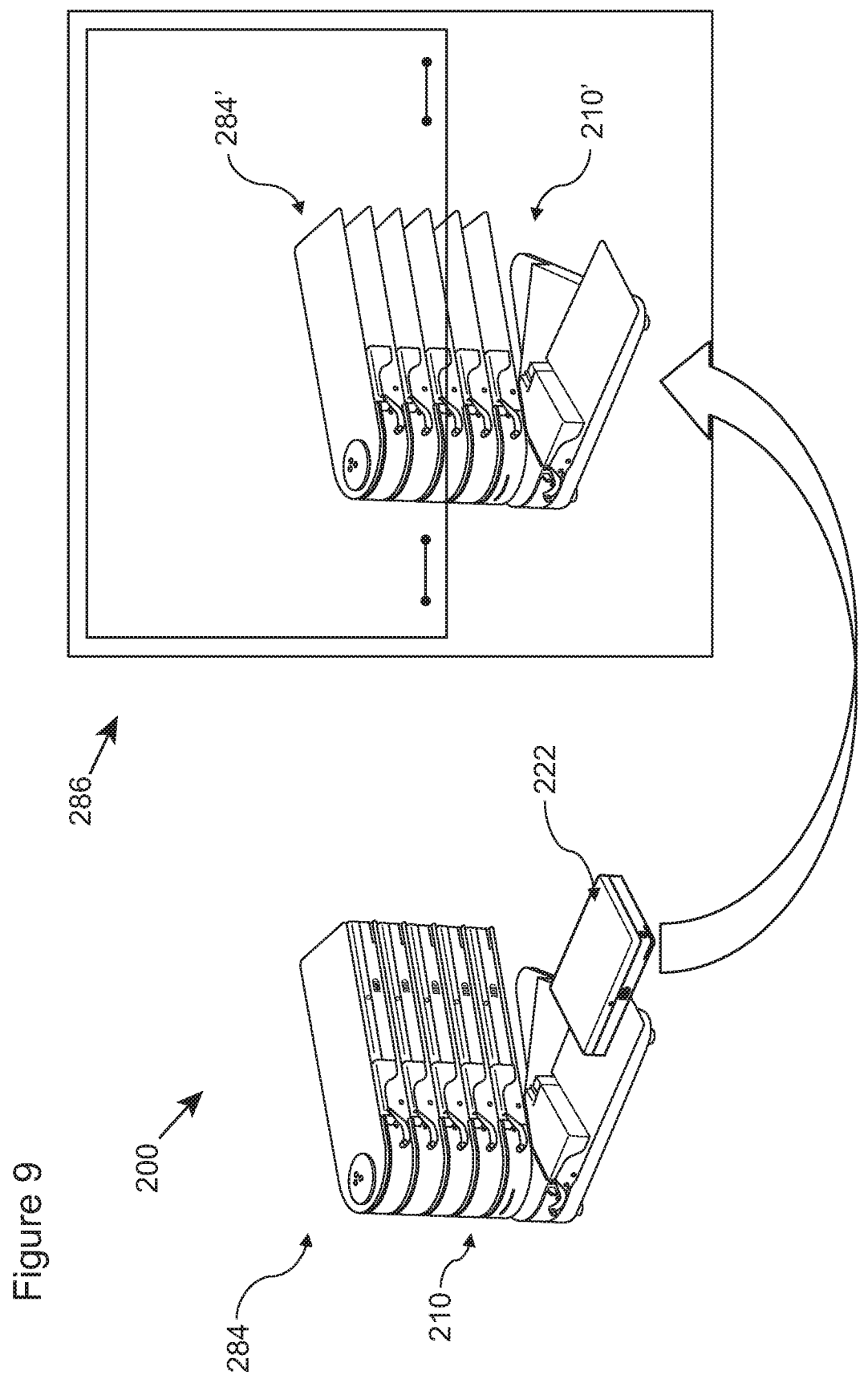
FIG. 9 shows a perspective representation of an incubator system in accordance with the third aspect of the invention, indicating the transfer of an incubator between first and second incubator docking systems in accordance with the second aspect of the invention.

An incubator system 200 is illustrated in FIG. 9, in which an incubator docking systems 284, 284' are provided. Each incubator docking system comprises at least an incubator stand 210, 210' and an incubator 222; and the incubator 222 may be shared between the two incubator docking systems 284, 284'. Each incubator stand 210, 210' is releasably couplable to its incubator or incubators 222, as per the first-described embodiment above.

The first incubator stand 284 is provided in normal working lab-space, such as on a benchtop, whereas the second incubator stand 284' is provided is a clean environment, such as a fume hood 286. The present incubator system 200 allows a user to transfer an incubator 222 between working environments without compromising the environmental conditions for samples inside the incubator 222. The incubator 222 can be decoupled from the first incubator stand 284 and transferred to the second incubator stand 284' inside the fume hood 286, and vice versa, at which point the incubator 222 can be re-coupled to a fluid and/or electricity supply.

It will be appreciated that the above-described systems could be provided such that only one or other of fluid and/or electricity is supplied to the incubator bases in each incubator docking system, and the skilled person will appreciate that it is not necessary for both the fluid conduit and electrical loom to be provided.

Whilst a triangular stand base is suggested, it will be appreciated that a number of different base arrangements could be provided with rotatable or pivotable incubator bases engaged with a shaft element. Provided that the stand base is sufficiently secured so as not to topple, then the docking system will be viable. Whilst this may be most readily achieved by providing a stand base in which the centre of mass is always directly above at least part of the stand base, regardless of a position of the incubator bases, it will be appreciated that a much wider angular range of movement of incubator bases could be achieved by fixing the stand base to a benchtop, for example, without using a specific stand base shape or size.

It is therefore possible to provide an incubator stand which is capable of pivotably supporting a plurality of incubators in a stack without toppling. This allows the incubators to be compactly stored with electrical and fluid supplies, and allows for ready interrogation of each incubator, when desired, whilst also potentially allowing for removal or transport of the incubators.

Whilst a preferable maximum angular displacement of each of the plurality of incubator bases of or substantially of 60 degrees, which matches or substantially matches an angular range of the triangular shape of the stand base, has been suggested it will be appreciated that other maximum angular displacements could be utilised which would similarly result in a stable system. The outer edge of the incubator base could have a maximum angular displacement which exceeds the projected width of the stand base, as long as the centre of mass of the system remains within the stand base. This would allow for a slightly larger range of movement of the stand base than previously suggested.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

What is claimed is:

1. An incubator stand for holding a plurality of incubators in a stacked arrangement, the incubator stand comprising:
   a stand base;
   a shaft upstanding from the stand base;
   a plurality of incubator bases rotatably received on the shaft, each incubator base forming a support for or forming part of an incubator;
   a stop coupled to the shaft and configured to limit angular displacement of each incubator base about the shaft, so that each incubator base can be pivoted out from a stack of said incubator bases to access an in use incubator associated therewith without causing the stack to topple; and
   a fluid-supply conduit which extends from the stand base;
   wherein each incubator base is a caddy for releasably receiving an incubator thereon;
   each caddy includes a fluid inlet port and a fluid outlet port in fluid communication with the fluid-supply conduit, and which are fluid-tightly releasably engagable with corresponding incubator ports on said incubator from the caddy;
   further comprising a fluid shut-off valve at or adjacent to the fluid inlet port and/or fluid outlet port, and a closure activation element which operates the fluid shut-off valve on release of the said incubator from the caddy.

2. The incubator stand as claimed in claim 1, wherein each incubator base has a maximum width which is less than a maximum width of the stand base, the stop preventing angular displacement of each incubator base beyond the maximum width of the stand base.

3. The incubator stand as claimed in claim 1, wherein the fluid-supply conduit upstands from the stand base at or adjacent to or substantially in parallel with the shaft.

4. The incubator stand as claimed in claim 1, wherein secondary conduits extend from the fluid-supply conduit to fluidly connect each incubator base with the fluid-supply conduit.

5. The incubator stand as claimed in claim 1, wherein the fluid-supply conduit is received within the stop.

6. The incubator stand as claimed in claim 1, further comprising an electrical-wiring loom which extends from the stand base.

7. The incubator stand as claimed in claim 6, wherein the electrical-wiring loom extends at or adjacent to the shaft.

8. The incubator stand as claimed in claim 6, wherein electrical spurs extend from the electrical-wiring loom to electrically connect each incubator base with the electrical-wiring loom.

9. The incubator stand as claimed in claim 6, wherein the electrical-wiring loom is received within the stop.

10. The incubator stand as claimed in claim 1, further comprising an electrical-wiring loom extending from the stand base, each caddy including at least one electrical connector in electrical communication with the electrical-wiring loom, the electrical connector being electrically releasably engagable with a corresponding connector of the said incubator from the caddy.

11. The incubator stand as claimed in claim 1, further comprising a releasable locking element for releasably engaging the caddy and an incubator, the releasable locking element comprising at least one hooked arm which is automatically latchable with a receiver on the said incubator.

12. The incubator stand as claimed in claim 1, wherein the stop defines a maximum angular displacement of each of the plurality of incubator bases of no more than 90 degrees.

* * * * *